US00PP14188P29

(12) United States Plant Patent
Hofmann

(10) Patent No.: US PP14,188 P2
(45) Date of Patent: Sep. 30, 2003

(54) VARIETY OF GERANIUM PLANT NAMED 'FIWOREWHI'

(50) Latin Name: *Pelargonium x hortorum (zonal geranium)*
Varietal Denomination: 'Fiworewhi'

(75) Inventor: Christa Hofmann, Grossdittmannsdorf (DE)

(73) Assignee: Elsner Pac Jungpflanzen (DE)

( * ) Notice: Subject to any disclaimer, the term of this patent is extended or adjusted under 35 U.S.C. 154(b) by 0 days.

(21) Appl. No.: 10/120,908

(22) Filed: Apr. 10, 2002

(51) Int. Cl.[7] ..... A01H 5/00
(52) U.S. Cl. ..... Plt./330

(58) Field of Search ..... Plt./330

(56) References Cited

PUBLICATIONS

GTITM UPOVRom Citation for 'Fiworewhi' as per Q2Z PBR 001478; Oct. 9, 2000.*

* cited by examiner

*Primary Examiner*—Kent Bell
(74) *Attorney, Agent, or Firm*—Webb Ziesenheim Logsdon Orkin & Hanson, P.C.

(57) ABSTRACT

A new and distinct zonal geranium plant named 'Fiworewhi' having red-orange colored flowers which exhibit lighter markings and having a star-like appearance as shown and described.

1 Drawing Sheet

Varietal denomination: 'Fiworewhi'.
Botanical classification: *Pelargonium×hortorum* (zonal geranium).

BACKGROUND OF THE INVENTION

The present invention comprises a new and distinct cultivar of geranium known by the varietal name 'Fiworewhi'. The new variety was discovered in a selective breeding program in Dresden, Germany. The new variety is the result of a combination breeding of unnamed, unpatented selections from breeding group 7K-34. The new variety exhibits the compact growth and branching of its heritage, but differs in its flower color. The new variety was first asexually reproduced by cuttings in Dresden, Germany in 1998. The new variety has been trial and field tested and has been found to retain its distinctive characteristics and remain true to type through successive propagations.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions via cuttings carried out in Dresden, Germany. The color readings were taken indoors on plants grown in 19 cm. pots in greenhouses during summer. Plants for the description were 9 months old. Color references are primarily to The R.H.S. Colour Chart of The Royal Horticultural Society of London.

PLANT

Form: Upright.
Height from media surface to top of foliage: 22–26 cm.

Height from media surface to top of umbels: 30–34 cm.
Time to produce a flowering plant: 16 weeks.
Growth: Erect, well branched.
Strength: Does not require artificial support.
Roots: White, adventive, 3.5 weeks to develop.
Leaves: Opposite arrangement; zone present.
- *Length.*—4 cm.
- *Width.*—6.5 cm.
- *Shape.*—Overall: Reniform. Base: Cordate. Apex: Pointed.
- *Margin.*—Bicrenate.
- *Texture.*—Hairy.
- *Color.*—Upper surface: 137B with zone of 147A. Lower surface: 147B.

Ribs and veins:
- *Venation.*—Net-veined.
- *Color.*—146B.

Petioles:
- *Color.*—146B.
- *Length.*—4.5 cm.

Stem/branches:
- *Color.*—146C.
- *Overall stem length.*—23–25 cm.
- *Internode length.*—1.5 cm.
- *Lateral branch length.*—18 cm.

THE BUD

When just beginning to open:
Shape:
- *Overall.*—Umbel-shaped.
- *Individual bud.*—Spindle-shaped.

Color: 43B.
Size:
- *Cluster.*—4 cm in diameter.
- *Individual bud.*—Length: 1.0 cm. Width: 0.5 cm.

INFLORESCENCE

Flowering: Continuous through summer until frost, flowers appear star-like from a distance.

Lasting quality:
*Individual flowers.*—8–10 days.
*Inflorescence.*—3–4 weeks.
Borne: Umbel; flowers on pedicel; pedicel on peduncle.
Umbel:
*Width.*—8 cm.
*Depth.*—4.5 cm.
*Number of flowers per umbel.*—35–40.
*Flowers.*—Form: Zygomorph, single.
*Size.*—Diameter: 3.5–4.0 cm. Depth: 1 cm.
*Petals.*—Color: Upper surface: 44C with eye of 43D. Lower surface: 44C. Quantity: 5 per flower. Size: Length: Upper petals: 2.5 cm. Lower petals: 2.0 cm. Width: Upper petals: 0.4 cm. Lower petals: 1.1 cm. Shape: Overall: Upper: Narrow/pointed. Lower: Oval. Apex: Upper: Pointed. Lower: Pointed. Base: Pointed. Margin: Serrated. Texture: Smooth.
Petaloids: Absent.
Sepals:
*Shape.*—Overall: Pointed, narrow. Apex: Pointed. Base: Fused.
*Color.*—Upper Surface: 144A. Lower Surface: 144A.
*Size.*—Length: 0.7 cm. Width: 0.2 cm.
Pedicel:
*Length.*—3.0–3.5 cm.
*Color.*—144B.
Peduncle:
*Length.*—12.5 cm.
*Color.*—144A.
Disease/pest resistance: No susceptibility to diseases or pests noted to date.

REPRODUCTIVE ORGANS

Stamens:
*Anthers.*—3 mm long.
*Filaments.*—Length: 4 mm. Color: 145D.
*Pollen.*—28A.
Pistils:
*Number.*—One, five parted.
*Length.*—2.5 mm.
*Stigma.*—11D.
*Style.*—Length: 0.5 cm. Color: 11D.
Ovaries: Superior, hairy.
*Length.*—0.4 cm.
*Color.*—138B.
Fruit: If present, maximum 5 per flower, 0.3–0.4 cm long, 165A.

GENERAL CHARACTERISTICS

1. Star-like appearance of flowers.
2. Reniform-shaped leaves.
3. Compact growth.
4. Single flowering.
5. Green zonation.
6. Good branching.
7. Rich in flowering.
8. Self-cleaning umbels.

I claim:

1. A new and distinct variety of geranium plant substantially as shown and described.

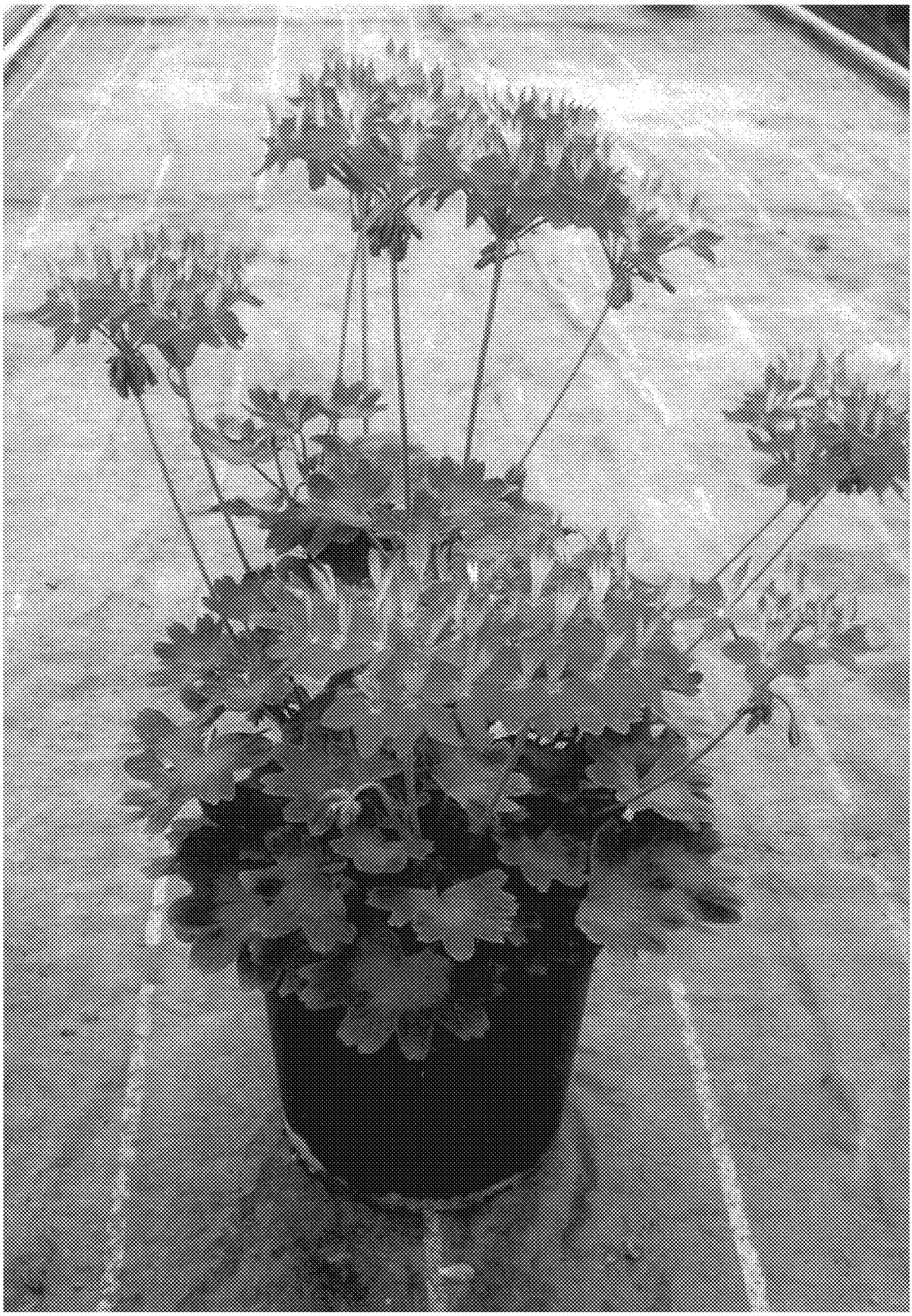

* * * * *